US00PP22621P2

(12) United States Plant Patent
Klemm et al.

(10) Patent No.: US PP22,621 P2
(45) Date of Patent: Apr. 3, 2012

(54) POINSETTIA PLANT NAMED 'NPCW10193'

(50) Latin Name: ***Euphorbia pulcherrima* Willd. ex Klotzsch**
Varietal Denomination: NPCW10193

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 11 days.

(21) Appl. No.: 12/925,835

(22) Filed: Oct. 29, 2010

(51) Int. Cl.
*A01H 5/00* (2006.01)

(52) U.S. Cl. ..... Plt./306

(58) Field of Classification Search ..... Plt./306
See application file for complete search history.

*Primary Examiner* — Susan McCormick Ewoldt

(74) *Attorney, Agent, or Firm* — Jondle & Associates, P.C.

(57) ABSTRACT

A new *poinsettia* plant named 'NPCW10193' particularly distinguished by its compact growth habit, late flowering season, slight torsian of the bracts and an apricot color, is disclosed.

1 Drawing Sheet

Genus and species: *Euphorbia pulcherrima* Willd. ex Klotzsch.
Variety denomination: 'NPCW10193'.

BACKGROUND OF THE NEW PLANT

The present invention comprises a new and distinct variety of *poinsettia* plant, botanically known as *Euphorbia pulcherrima* Willd. ex Klotzsch and hereinafter referred to by the variety name 'NPCW10193'. The new variety is the result of a natural pollination between November 2006 and January 2007 in Kenya between unknown parents. A single plant selection was subsequently chosen for further evaluation and asexual propagation.

'NPCW10193' was first propagated via vegetative cuttings and has been asexually reproduced by vegetative cuttings in Stuttgart, Germany for over six generations. 'NPCW10193' has been found to retain its distinctive characteristics through successive asexual propagations via vegetative cuttings.

'NPCW10193' has not been sold or made publicly available more than one year prior to the filing date of this application.

SUMMARY OF THE INVENTION

The following are the most outstanding and distinguishing characteristics of this new variety when grown under normal horticultural practices in Stuttgart, Germany.

1. Compact growth habit;
2. Slight torsian of the bracts; and
3. Apricot color.

DESCRIPTION OF THE PHOTOGRAPH

This new *poinsettia* plant is illustrated by the accompanying photograph which shows overall plant habit including blooms, and foliage of the plant; the colors shown are as true as can be reasonably obtained by conventional photographic procedures. The photograph is of a whole plant about four-months-old and in full flower.

DESCRIPTION OF THE NEW VARIETY

The following detailed description sets forth the distinctive characteristics of 'NPCW10193'. The data which define these characteristics were collected from asexual reproductions carried out in Stuttgart, Germany. The plant history was taken on four month-old plants grown in 13 cm pots from August to December 2009 with a minimum pinch date of 32 weeks. The plants were grown in a greenhouse covered with glass. Color readings were taken under natural light in the greenhouse. Color references are primarily to The R.H.S. Colour Chart of The Royal Horticultural Society of London (R.H.S.) (5$^{th}$ edition 2007).

DETAILED BOTANICAL DESCRIPTION OF THE NEW PLANT

Classification:
- *Family.*—Euphorbiaceae.
- *Botanical.*—*E. pulcherrima* Willd. ex Klotzsch.
- *Common.*—Poinsettia.

Parentage: Unknown

Growth:
- *Time to produce a rooted cutting.*—3 to 4 weeks.
- *Blooming habit.*—Intermittent; blooms from end of November to January.
- *Flowering response time.*—Approximately 55 days from beginning of short-days until flowering.
- *Keeping quality.*—Very good.

Plant:
- *Form.*—Triangular.
- *Growth habit.*—Upright.
- *Height.*—20.0 cm to 25.0 cm.
- *Width.*—20.0 cm to 30.0 cm.
- *Number of branches.*—5 to 7.
- *Average number of inflorescences per plant.*—5 to 7.

Stems:
- *Color.*—Lower part: RHS 135B. Upper part: RHS 142C.
- *Length.*—About 20.0 cm.
- *Internode length.*—1.0 cm to 3.0 cm.
- *Diameter.*—0.5 cm to 1.0 cm.

Leaves:
- *Quantity.*—6 to 10 per lateral branch.
- *Arrangement.*—Alternate.
- *Shape.*—Ovate.

*Apex.*—Acuminate.
*Base.*—Truncate.
*Margin.*—Serrate.
*Lobes.*—Very few. Lobation characteristics: Shallow.
*Texture* (*both surfaces*).—Smooth.
*Vein color* (*both surfaces*).—RHS 135D.
*Variegation.*—Absent.
*Size.*—Length: 6.0 cm to 14.0 cm. Width: 4.0 to 8.0 cm.
*Color.*—Mature foliage: Upper surface: RHS 136A. Lower surface: RHS N138B. Immature foliage: Upper surface: RHS 143B. Lower surface: RHS 143C.
*Leaf petiole.*—Length: 2.0 cm to 4.0 cm. Diameter: 0.2 cm to 0.3 cm. Color (both surfaces): RHS 144D.

Inflorescence:
*Lastingness of inflorescence on the plant.*—3 to 4 weeks.
*Diameter.*—12.0 cm to 20.0 cm.
*Height.*—2.0 to 3.0 cm.

Bracts:
*Number of bracts per inflorescence.*—About 8.
*Shape.*—Ovate.
*Apex.*—Acuminate.
*Base.*—Rounded.
*Margin.*—Few lobes.
*Size.*—Length: 6.0 cm to 12.0 cm. Width: 3.0 cm to 6.0 cm.
*Texture* (*both surfaces*).—Smooth.
*Vein color* (*both surfaces*).—RHS 144D.
*Bract color.*—Upper surface: RHS 18C, spots RHS 47C. Lower surface: RHS 18C, spots RHS 47C (less visible on lower surface).
*Bract petiole.*—Length: 1.0 cm to 2.0 cm. Diameter: 0.2 cm. Color (both surfaces): RHS 144D.

Cyme:
*Diameter.*—1.0 cm to 1.5 cm.
*Cyathia number.*—5 to 6 per inflorescence.
*Cyathium.*—Shape: Ovate. Diameter: 0.2 cm to 0.4 cm. Length: 0.3 cm to 0.5 cm. Color: RHS 135B.
*Peduncle.*—Color: RHS 142C. Length: 0.1 cm to 0.2 cm.
*Nectar cups.*—Number: 1 per cyathia. Diameter: 0.1 cm when closed, 0.2 cm when open. Size: 0.2 to 0.4 cm. Color: RHS 142C.

Reproductive organs:
*Stamens.*—Shape: Ovate.
*Pollen.*—Quantity: Sparse. Color: RHS 11A.
*Filament color.*—RHS 1D.
*Gynoecium.*—Present.

Fruit and seed set: No fruit or seed have been observed
Disease and insect/pest resistance: Good

COMPARISON WITH COMMERCIAL VARIETY

'NPCW10193' differs from the commercial variety 'Cinnamon Star' (U.S. Plant Pat. No. 16,964) by being more compact and flowering later, while 'Cinnamon Star' is more vigorous and flowers earlier.

We claim:

1. A new and distinct variety of *poinsettia* plant named 'NPCW10193' as described and shown herein.

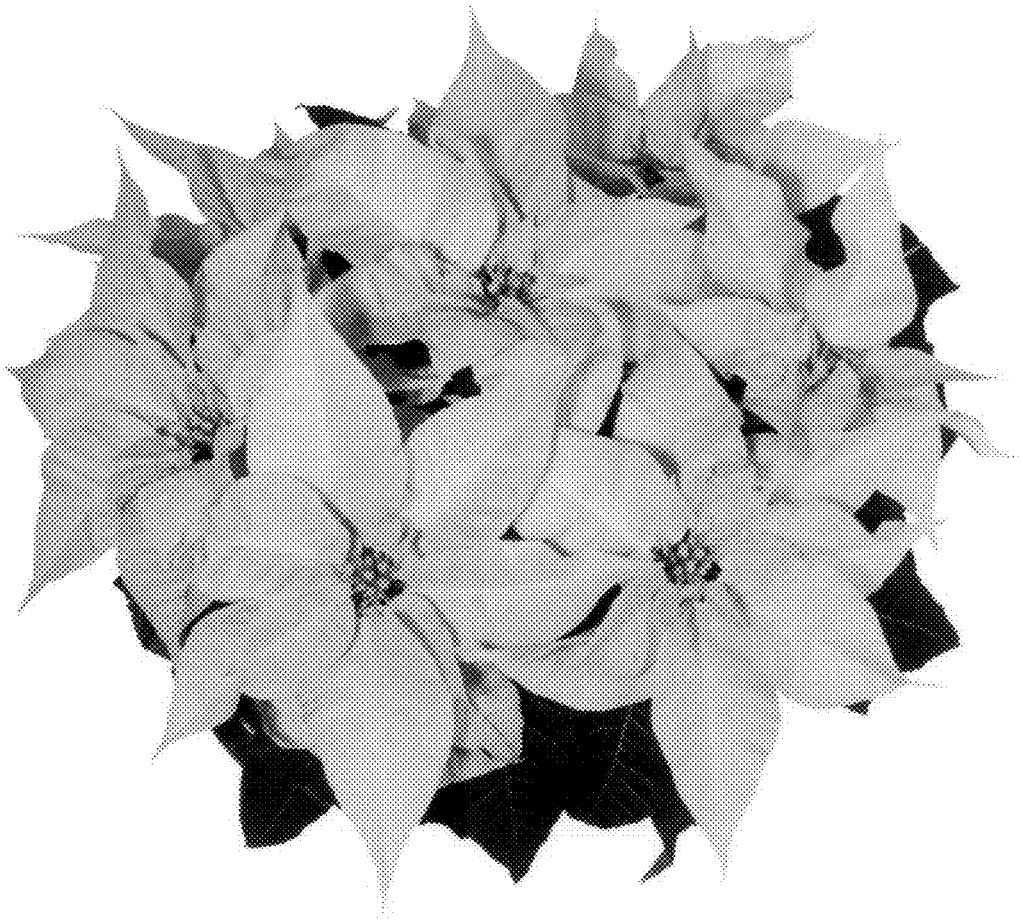

* * * * *